United States Patent [19]
Reddy et al.

[11] Patent Number: 5,574,146
[45] Date of Patent: Nov. 12, 1996

[54] OLIGONUCLEOTIDE SYNTHESIS WITH SUBSTITUTED ARYL CARBOXYLIC ACIDS AS ACTIVATORS

[75] Inventors: M. Parameswara Reddy; Firdous Farooqui, both of Brea, Calif.

[73] Assignee: Beckman Instruments, Inc., Fullerton, Calif.

[21] Appl. No.: 298,545

[22] Filed: Aug. 30, 1994

[51] Int. Cl.$^6$ .................. C07H 21/00; C07H 21/04; C07H 1/00
[52] U.S. Cl. ............... 536/25.34; 536/26.1; 536/55.3
[58] Field of Search ................ 536/26.1, 25.34, 536/55.3

[56] References Cited

FOREIGN PATENT DOCUMENTS

0649855A1  10/1994  Germany.
WO89/09779  10/1989  WIPO.

OTHER PUBLICATIONS

Mateucci et al. Tetrahedron Lett. 24:3171–3174, 1983.
Pon, R. T. Tetrahedron Lett. 28:3643–3646, 1987.
Wright, P. et al. Tetrahedron Lett. 34:3373–3376, 1993.
Fourrey et al. Tetrahedron Lett. 25: 4511–4514, 1984.
Fourrey et al. Tetrahedron Lett. 28: 1769–1772, 1987.
Arnold et al. Collect. Czech. Chem. Commun. 54: 523–532, 1989.
Stec et al. Tetrahedron Letters 25: 5279–5282, 1984.
Hering et al. Nucleosides & Nucleotides 4: 169–171, 1985.
Conte, Maria R., et al; "Solid Phase Synthesis of 5–Hydroxymethyluracil Containing DNA", Bioorganic & Medicinal Chemistry Letters, vol. 2, No. 1, pp. 79–82, 1992.
Beaucage, Serge L., et al; "Advances in the Synthesis of Oligonucleotides by the Phosphoramidite Approach"; Tetrahedron Report No. 309; Tetrahedron vol. 48, No. 12, pp. 2223–2311, 1992.

Primary Examiner—Gary L. Kunz
Attorney, Agent, or Firm—William H. May; Janis C. Henry

[57] ABSTRACT

A process for synthesizing oligonucleotides by phosphoramidite chemistry wherein the improvement is the use of substituted aryl carboxylic acids as the activators. These activators produce in situ nucleotide intermediates in which the substituted arylcarbonyl group has displaced the amidite moiety.

13 Claims, No Drawings

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:1:

CTGGACACTA GTCCGACTGC T    21

( 2 ) INFORMATION FOR SEQ ID NO:2:

( i ) SEQUENCE CHARACTERISTICS:
      ( A ) LENGTH: 10 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:2:

TCCGACAGCT    10

( 2 ) INFORMATION FOR SEQ ID NO:3:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA (genomic)

(xi) SEQUENCE DESCRIPTION: SEQ ID NO:3:

TACTGTAGGC AGTACGAGAG T 21

(2) INFORMATION FOR SEQ ID NO:4:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:4:

AGTCAGTCAG TCAGTCAGTC AGTCT 25

(2) INFORMATION FOR SEQ ID NO:5:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:5:

ACTCTCGTAC TGCCTACAGT A 21

OLIGONUCLEOTIDE SYNTHESIS WITH SUBSTITUTED ARYL CARBOXYLIC ACIDS AS ACTIVATORS

BACKGROUND OF THE INVENTION

The present invention relates generally to the fields of organic chemistry and biology. In particular, the present invention is directed to compositions and methods for use in oligonucleotide synthesis.

Phosphoramidite chemistry [*Beaucage, S. L. and Iyer, R. P. Tetrahedron* 48, 2223–2311 (1992)] has become by far the most widely used coupling chemistry for the synthesis of oligonucleotides. As is well known to those skilled in the art, phosphoramidite synthesis of oligonucleotides involves activation of nucleoside phosphoramidite monomer precursors by reaction with an activating agent to form activated intermediates, followed by sequential addition of the activated intermediates to the growing oligonucleotide chain (generally anchored at one end to a suitable solid support) to form the oligonucleotide product. Tetrazole is commonly used for the activation of the nucleoside phosphoramidite monomers; the activation occurs by the mechanism depicted in Scheme I. Tetrazole has an acidic proton which presumably protonates the basic nitrogen of the diisopropylamino phosphine group, thus making the diisopropylamino group a leaving group. The negatively charged tetrazolium ion then makes an attack on the trivalent phosphorous, forming a transient phosphorous tetrazolide species. The 5'—OH group of the solid support bound nucleoside then attacks the active trivalent phosphorous species, resulting in the formation of the internucleotide linkage. The trivalent phosphorous is finally oxidized to the pentavalent phosphorous.

Scheme I

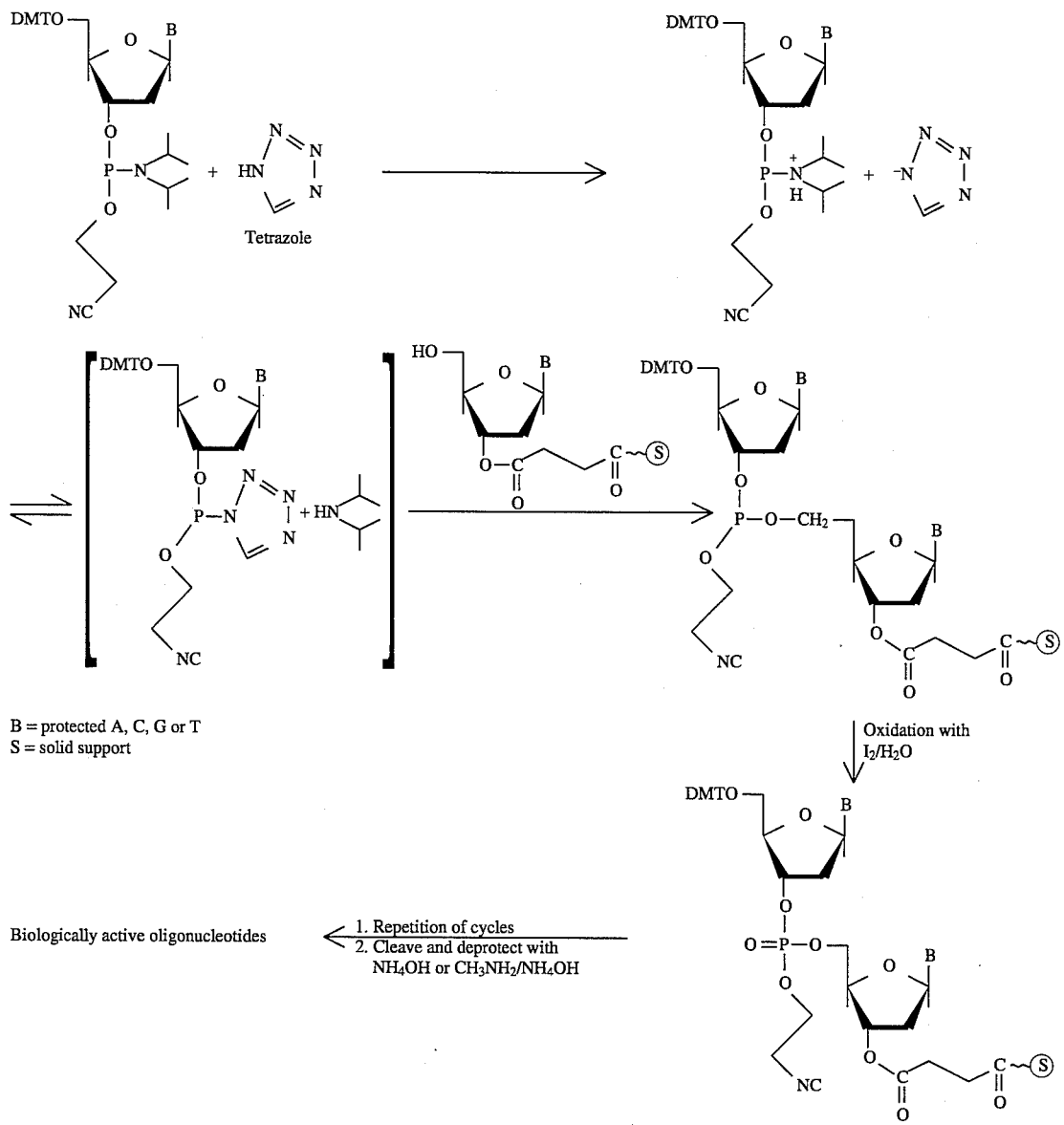

B = protected A, C, G or T
S = solid support

Biologically active oligonucleotides ⇐ 1. Repetition of cycles
2. Cleave and deprotect with NH₄OH or CH₃NH₂/NH₄OH A principal drawback of tetrazole is its cost. It is the second most expensive reagent in oligonucleotide synthesis, costing about 40–50% the price of the nucleoside phosphoramidite. Because of the inherent instability of this highly nitrogenous heterocyclic compound, moreover, sublimed tetrazole is generally required to ensure desired coupling yields. Further, tetrazole (which is typically used near its saturated solubility of 0.5M) tends to precipitate out of acetonitrile solution at cold temperatures; this can lead to valve blockage on some automated DNA synthesizers.

Other activators which work almost as efficiently as tetrazole have similar drawbacks to those of tetrazole as discussed above. These activators include the following members of the tetrazole class of activators: 5-(p-nitrophenyl) tetrazole [Froehler, B. C. & Matteucci, M. D., *Tetrahedron Letters* 24, 3171–3174 (1983)]; 5-(p-nitrophenyl) tetrazole+DMAP [Pon, R. T., *Tetrahedron Letters* 28, 3643–3646 (1987); and 5-(ethylthio)-1-H-tetrazole [Wright, P. et al., *Tetrahedron Letters* 34, 3373–3376 (1993)]. In addition to the tetrazole class of activators, the following activators have been employed: N-methylaniline trifluoroacetate [Fourray, J. L. & Varenne, J., *Tetrahedron Letters* 25, 4511–4514 (1984)]; N-methyl anilinium trichloroacetate [Fourrey, J. L. et al., *Tetrahedron Letters* 28, 1769–1772 (1987)]; 1-methylimidazoletrifluoromethane sulfonate [Arnold, L. et al., *Collect. Czech. Chem. Commun.* 54, 523–532 (1989)]; octanoic acid or triethylamine [Stec, W. J. & Zon, G., *Tetrahedron Letters* 25, 5279–5282 (1984)]; 1-methylimidazole. HCl, 5-trifluoromethyl-1H-tetrazole, N,N-dimethylaniline. HCl and N,N-dimethylaminopyridine. HCl [Hering, G. et al., *Nucleosides and Nucleotides* 4, 169–171 (1985)]. Overall, these activators gave inferior performance relative to tetrazole.

It is an object of the present invention to provide activated nucleosides for use in solid phase synthesis which do not exhibit all of the drawbacks of the prior art compositions.

It is a further object of the present invention to provide methods for the preparation and use of activated nucleosides as hereinafter described.

SUMMARY OF THE INVENTION

In accordance with the present invention, there are provided activated nucleoside derivatives formed in situ of general formula I

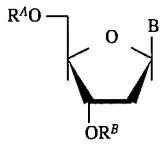

in which one of $R^A$ and $R^B$ is $R^3$ and the other is

$-P(R_2)OR^1$ wherein $R^1$ is a substituted arylcarbonyl group (as hereinafter defined), $R^2$ is selected from the group consisting of $R^4O$ and $R^5$ (as hereinafter defined), $R^3$ is a hydroxyl-protecting group (as hereinafter defined) and B is a purine or pyrimidine base. Particularly preferred are those compounds wherein $R^1$ is 2,4-dinitrophenylcarbonyl. In accordance with a further aspect of the present invention, these compounds are prepared using the corresponding carboxylic acids; these acids are generally more soluble in acetonitrile (for example, to the extent of 1.5 M for 2,4-dinitrobenzoic acid) than tetrazole and work as activators at lower concentrations. These compounds are about 10 times less expensive to prepare compared to the corresponding tetrazole compounds.

DETAILED DESCRIPTION OF THE INVENTION

Pursuant to a first aspect of the present invention, compounds of general formula I

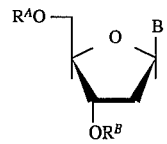

in which one of $R^A$ and $R^B$ is $R^3$ and the other is

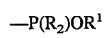

$-P(R_2)OR^1$ wherein $R^1$ is a substituted arylcarbonyl group, $R^2$ is selected from the group consisting of $R^4O$ and $R^5$, $R^3$ is a hydroxyl-protecting group and B is a purine or pyrimidine base, are provided.

For purposes of the present invention, by "substituted arylcarbonyl group" is meant an aryl group bearing at least one electron-withdrawing substituent which does not interfere with the oligonucleotide synthesis reaction ("a non-interfering substituent") attached to a carbonyl (C=O) group. Suitable aryl groups include, but are not limited to, phenyl, naphthyl and anthracyl; phenyl is presently preferred. Suitable non-interfering substituents include, but are not limited to, halogen (i.e., chloro, bromo, fluoro and iodo) and nitro. Preferred $R^1$ groups include the following: 2-nitrophenylcarbonyl; 3,5-dinitrophenylcarbonyl; 2,4,5-trifluorophenylcarbonyl; 2,3,6-trifluorophenylcarbonyl; 2,3,6-trifluorophenylcarbonyl; 2,3,5,6-tetrafluorophenylcarbonyl; pentafluorophenylcarbonyl; 3-nitrophenylcarbonyl; and 2,4-dinitrophenylcarbonyl. Particularly preferred is 2,4-dinitrophenylcarbonyl.

One class of compounds of the general formula I of interest in accordance with the present invention are those wherein $R^2$ has the formula $R^4O-$. In this class of compounds, suitable $R^4$ groups include but are not limited to the following: lower alkyl (which for purposes of the present invention is defined as straight- or branched-chain alkyl of one to about five carbon atoms); $NCCH_2CH_2-$; $NCCH_2CHMe-$; $CNCH_2CMe_2-$; $Cl_3CCH_2-$; $Cl_3CCHMe-$; $Cl_3CCMe_2-$; $C_6H_5SO_2CH_2CH_2-$; $MeSO_2CH_2CH_2-$; and $NO_2C_6H_4CH_2CH_2-$ [see, e.g., Beaucage & Iyer, supra, pp. 2280–2281]. The compounds of general formula I are prepared in a manner as hereinafter described from the corresponding compounds of general formula II

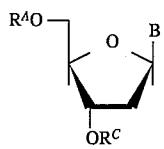

in which one of $R^A$ and $R^C$ is $R^3$ and the other is

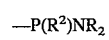

$-P(R^2)NR_2$ wherein B, $R^2$ and $R^3$ are as previously defined and each R is lower alkyl (preferably, isopropyl) or both R taken together from the group —$(CH_2)_2$—O—$(CH_2)_2$—. The compounds of general formula II are commercially available and/or may be prepared in a manner known per se.

Another class of compounds of interest in accordance with the present invention are those of general formula I wherein $R^2$ is $R^5$, in which $R^5$ is lower alkyl. This class includes in particular the compounds wherein $R^5$ is methyl (to provide methylphosphonate compounds). These compounds are particularly useful for preparing antisense oligonucleotides. Antisense nucleic acids offer an attractive potential alternative to conventional drugs [Uhlmann, E. & Peyman, A., *Chemical Reviews* 90, 543–584 (1990); Goodchild, J., *Bioconjugate Chemistry* 1, 165–187 (1990)]. They are designed to bind to specific target nucleic acid sequences of cellular or viral origin and regulate gene expression. Oligonucleoside methylphosphonates are one of the important classes of antisense nucleic acids which are being actively investigated at this time. The synthesis of this class of compounds using the exemplary 2,4-dinitrobenzoic acid and the mechanism of activation are depicted in Scheme II. Heterogeneous 10mers and 21mers synthesized using 2,4-dinitrobenzoic acid or tetrazole were virtually indistinguishable on reverse phase HPLC. In both cases, the oligonucleotide was cleaved and deprotected using ethylenediamine [Miller, P. S. et al., *Biochemistry* 25, 5092–5097 (1986)]. These compounds are also prepared from the corresponding compounds of general formula II, which are commercially available and/or may be prepared in a manner known per se.

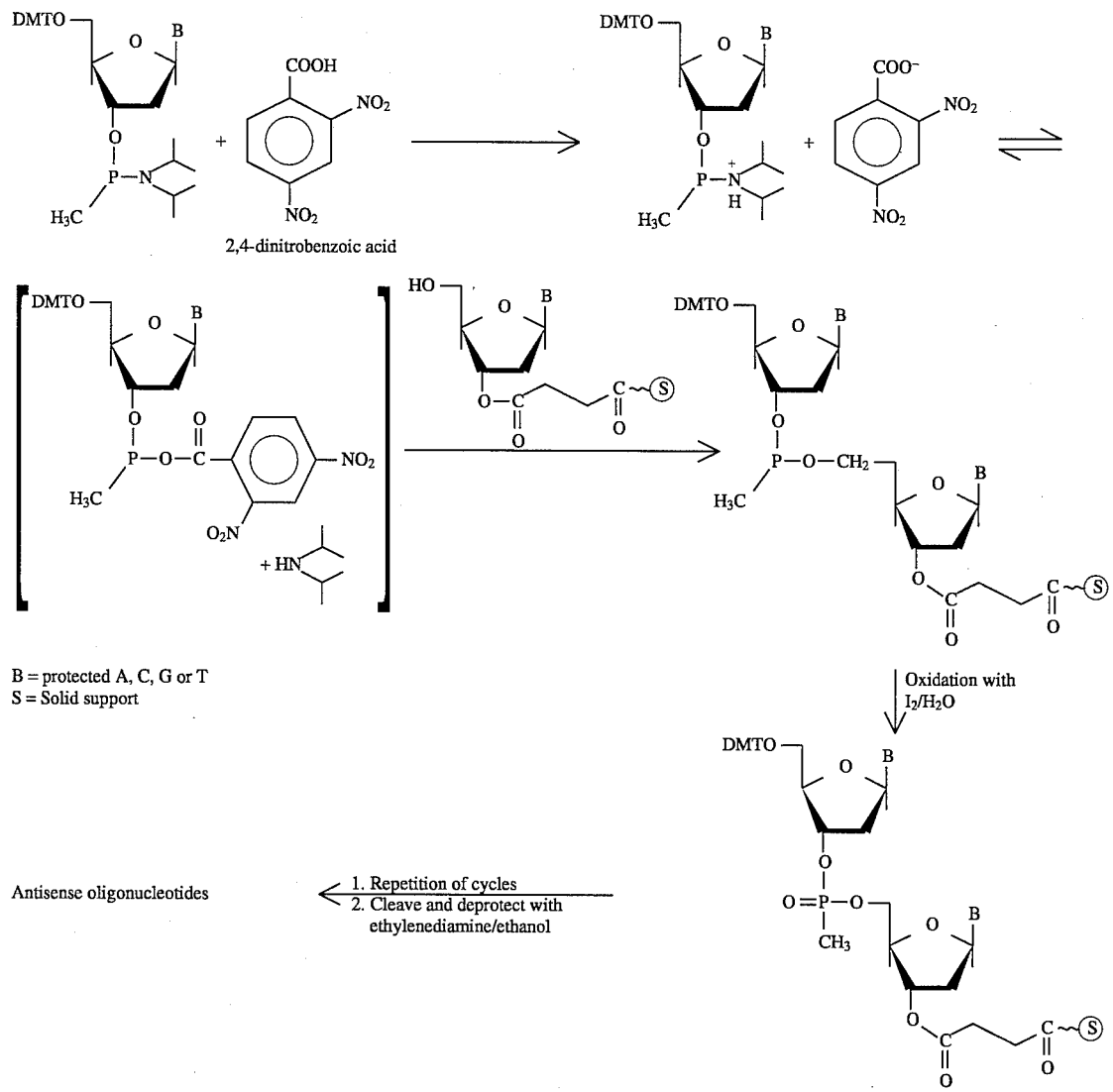

Scheme II

In the compounds of general formula I, $R^3$ is a hydroxyl-protecting group. By hydroxyl-protecting group is meant a radical which protects the hydroxyl substituent during the synthesis of polynucleotides or attachment of nucleotides to solid supports, but is readily removed at the end of nucleotide synthesis. For purposes of the present invention, the 4,4'-dimethoxytrityl (DMT) group is particularly preferred. Other suitable groups for protecting the 3'- or 5'-hydroxyl include, but are not limited to, the following: 4,4',4"-tris-(benzyloxy)trityl (TBTr); 4,4',4"-tris-(4,5-dichlorophthalimido)trityl (CPTr); 4,4',4"-tris(levulinyloxy)trityl (TLTr); 3-(imidazolylmethyl)-4,4'-dimethoxytrityl (IDTr); pixyl (9-phenylxanthen-9-yl); 9-(p-methoxyphenyl)xanthen-9-yl (Mox); 4-decyloxytrityl ($C_{10}Tr$); 4-hexadecyloxytrityl ($C_{16}GTr$); 9-(4-octadecyloxyphenyl)xanthene-9-yl ($C_{18}Px$); 1,1-bis-(4-methoxyphenyl)-1'-pyrenyl methyl (BMPM); p-phenylazophenyloxycarbonyl (PAPoc); 9-fluorenylmethoxycarbonyl (Fmoc); 2,4-dinitrophenylethoxycarbonyl (DNPEoc); 4-(methylthiomethoxy)butyryl (MTMB); 2-(methylthiomethoxymethyl)-benzoyl (MTMT); 2-(isopropylthiomethoxymethyl)benzoyl (PTMT); 2-(2,4-dinitrobenzenesulphenyloxymethyl)benzoyl (DNBSB); and levulinyl groups. These and other suitable protecting groups are described in detail in Beaucage & Iyer, supra, the entire disclosure of which is hereby incorporated by reference.

For purposes of the present invention, B in general formulas I and II represents a pyrimidine or purine base. Preferred for use in accordance with the present invention are those bases characteristic of guanine, adenine, thymine and cytosine; however, other purine or pyrimidine bases as may be employed in the synthesis of nucleotide analogs may alternatively be used as group B.

Pursuant to another aspect of the present invention, a method for the preparation of a compound of general formula I is provided. The preparation of a compound of general formula I by reaction of a corresponding compound of general formula II with a carboxylic acid of general formula $$R^1—OH$$

may be effected in a variety of solvents over a wide range of temperatures and for varying lengths of time, as would be readily appreciated by those skilled in the art. For any particular combination of compound of general formula II and carboxylic acid, optimum conditions may readily be determined empirically. In general, suitable solvents include, but are not limited to the following: acetonitrile, dioxane, tetrahydrofuran, dichloromethane and dimethylformamide. A particularly preferred solvent is acetonitrile, which is generally accepted by those working in the field as the optimal solvent for use in phosphoramidite coupling reactions. The reaction is generally carried out at a temperature of about 10° C. to about 60° C., and preferably at about room temperature. Depending on the temperature at which the reaction is carried out, the reaction is generally completed in a period of about 2 seconds to about 24 hours; at room temperature, the reaction typically takes about 5 seconds to about 3 hours. The reaction is typically carried out using at least about one stoichiometric equivalent of the carboxylic acid as compared to the compound of general formula II; preferably, an at least about two-fold excess to an about 100-fold excess of the carboxylic acid relative to the compound of general formula II would be employed.

It is a particular advantage of the present invention that the activated nucleoside intermediates of general formula I need not be isolated from the reaction mixture prior to use in oligonucleotide synthesis. Rather, the activated intermediate as formed in situ may be directly employed in the coupling reaction which results in the formation of the desired oligonucleotide product.

It is a further advantage of the present invention that the carboxylic acids employed in accordance with the present invention as activators to form the compounds of general formula I do not interfere with the stability of the hydroxyl-protecting group $R^3$ used to protect the 5'- or 3'-OH group of the nucleoside. As generally known by those working in the field, dichloro- or trichloroacetic acid (typically, approximately 0.2 M in a suitable solvent, such as dichloromethane) is employed to remove the protecting group $R^3$ after each synthesis cycle by a mechanism involving protonation of the oxygen. Although it was determined experimentally that both 0.05 M dichloroacetic acid and 0.05 M trichloroacetic acid could be employed as activators, it was further determined that dichloroacetic acid at this concentration removed 0.1% of the dimethoxytrityl protecting group and trichloroacetic acid removed 0.2% of the protecting group. This degree of deprotection would clearly be unacceptable in an oligonucleotide synthesis. In contrast, the carboxylic acids employed in accordance with the present invention removed only approximately 0.01% of the protecting group; this value, moreover, may in fact simply reflect a base line reading without any practical significance. In addition, it is speculated that interference with the protecting group may explain why octanoic acid and N-methylanilinium trichloroacetate (as proposed in the prior art) were found unsuitable for use as activating agents.

Pursuant to yet another aspect of the present invention, an improved method of oligonucleotide synthesis is provided in which a compound of general formula I is employed as an activated intermediate which is sequentially added to the growing oligonucleotide chain to form the desired oligonucleotide product. The oligonucleotides synthesized using activated intermediates of general formula I have been successfully used in various applications such as DNA amplification by polymerase chain reaction and DNA sequencing by dideoxy termination method. In addition, the compositions and methods of the present invention may be employed to prepare oligonucleoside phosphorothioates (another important class of antisense nucleic acids) as shown in Scheme III.

Scheme III

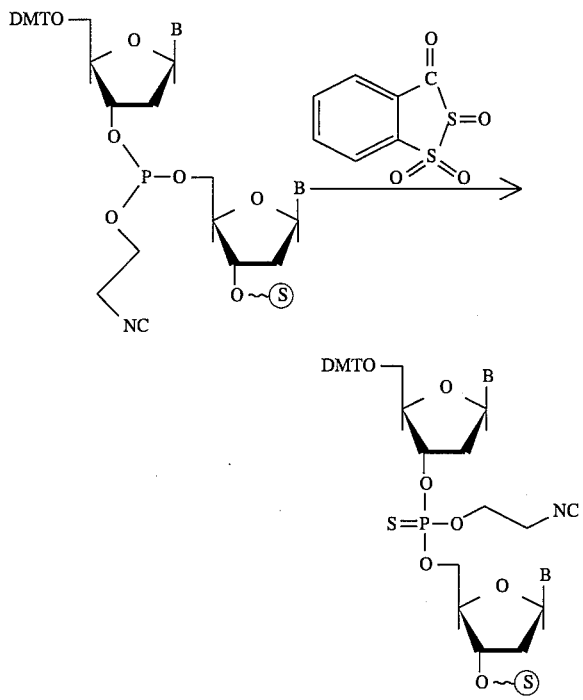

Beaucage reagent [Iyer, R. P. et al., *J. Amer. Chem. Soc.* 112, 1253–1254 (1990)] is used for sulfurization reaction. As confirmed by reverse phase HPLC analysis, oligonucleoside phosphorothioates synthesized using 2,4-dinitrobenzoic acid are comparable to those synthesized using tetrazole.

The invention may be better understood with reference to the accompanying examples, which are intended for pur-

EXAMPLE 1

Synthesis of Activated Nucleosides In Situ

5'-DMT-thymidine 3'-cyanoethyl phosphoramidite (5 mg, 0.007 mmole; obtained from Beckman Instruments, Fullerton, Calif.) was dissolved in 500 μl of $CD_3CN$ (obtained from Aldrich, Milwaukee, Wis.) in an NMR tube. The $^{31}P$ NMR spectrum was recorded on a Brucker 300 MHz spectrometer. The sample showed a resonance signal at 151.649 ppm. To this sample was then added 2,4-dinitrobenzoic acid (7.2 mg, 0.034 mmole; obtained from Aldrich) and the spectrum recorded after 2 minutes. The $^{31}P$ signal shifted to 136.716 ppm, indicative of the formation of the active species of general formula I. This was further confirmed by adding thymidine 3'-acetate (5 mg, 0.02 mmole; obtained from Sigma, St. Louis, Mo.) to the NMR tube. After 5 minutes, formation of the dinucleotide was confirmed by a $^{31}P$ signal appearing at 143.298 ppm.

EXAMPLE 2

Synthesis of a 21 mer oligonucleotide

A 21mer was synthesized on the Pharmacia DNA synthesizer (Pharmacia LKB Biotechnology, Piscataway, N.J.) using phosphoramidite chemistry. The 21 mer had the following sequence:

5' CTGGACACTAGTCCGACTGCT 3'    (SEQ ID NO:1)

For the above sequence, T-CPG solid support was used (0.2μ mole). Total cycle time was 9 minutes, with a coupling time of 4 minutes. The concentration of activator was 0.5 M in acetonitrile for tetrazole and 0.05 M in acetonitrile for 2,4-dinitrobenzoic acid. After synthesis was completed, the last DMT group was removed. The coupling efficiencies were in the range of 98–99%. The oligo was cleaved from solid support using ammonia for 1 hour at room temperature or using methylamine/ammonia reagent for 5 minutes at room temperature and deprotected for 3 hours at 65° C. with ammonia or 5 minutes at 65° C. with methylamine/ammonia [Reddy, M. P. et al., *Tetrahedron Letters* 35, 4311 (1994)]. The solution was concentrated on speed vacuum and analyzed on a Beckman 2000 P/ACE capillary gel electrophoresis system. The capillary gel column was a U100P urea Gel column (Cat. #338480 from Beckman Instruments, Fullerton, Calif.) and was loaded and cut to 37 cm long. A Tris-Borate, 7M Urea buffer (also from Beckman, Gel buffer Kit Cat. #338481 ) was used according to directions. The absorbances of the oligonucleotides were in the range of 0.05 to 2 $OD_{260nm}$/ml, depending upon the quality and length of oligonucleotides. Injection was at 10 kV for 3 sec, while separation was at 11 kV for 30–90 min, depending upon length. The electropherograms for both products were virtually indistinguishable.

EXAMPLE 3

Synthesis of Oligonucleoside methylphosphonates

The following 10mer and 21mer oligonucleoside methylphosphonate sequences were synthesized on Pharmacia DNA synthesizer:

10 mer: 5' TCCGACAGCT 3'    (SEQ ID NO:2)

21 mer: 5' TACTGTAGGCAGTACGAGAGT 3'    (SEQ ID NO:3).

The literature procedure was followed [Agarwal, S. & Goodchild, J., *Tetrahedron Letters* 28, 3539 (1987)]. Total cycle time was 10 minutes, with a coupling time of 5 minutes. The C and G methylphosphonamidites were dissolved in either dry DMF or dry THF, whereas the A and T methylphosphonamidites were dissolved in dry acetonitrile. The concentration of tetrazole and 2,4-dinitrobenzoic acid were 0.5 M and 0.05 M, respectively. The support used was T-CPG, 0.2 μmole. The coupling efficiencies were in the range of 97–98%. The last DMT group was left in place. The oligonucleoside methylphosphonate was cleaved and deprotected with ethylenediamine/ethanol (1:1) for 7 hours at room temperature. The samples were injected onto a reverse phase HPLC column for analysis under the following conditions: $C_{18}$ Ultrasphere column (Rainin), 5μ particles, 4.6 mm×25 cm; Bottle A: 0.01 M ammonium acetate (pH 6.9); Bottle B: Acetonitrile; Program: Flow rate 1 ml/min, 0–25 min gradient to 50% B, 25–27 min at 50% B, 27–30 min gradient to 0% B, 30–32 min at 0% B.

EXAMPLE 4

Synthesis of oligonucleoside phosphorothioates

The following oligonucleoside 25mer sequence was synthesized on a Pharmacia Instrument on T-CPG solid support (0.2 μmole):

5' AGTCAGTCAGTCAGTCAGTCAGTCT 3'    (SEQ ID NO:4).

The total cycle time was 9 minutes with coupling time of 4 minutes. The concentrations of tetrazole and 2,4-dinitrobenzoic acid were 0.5 M and 0.05 M, respectively. For sulfurization, 3H-1,2-benzdithiole-3-one 1,1-dioxide (Beaucage reagent) was used; 1 g of sulfurization reagent was dissolved in 100 mL of dry acetonitrile. Oxidation was performed for 30 seconds; the last DMT group was left in place. The coupling efficiencies were in the range of 98.75 to 99.6%. The oligonucleoside phosphorothioates were cleaved with either ammonia or methylamine/ammonia as described in Example 2. The thioates were analyzed by reverse phase HPLC and Beckman P/ACE 2000 using a gel filled capillary as previously described; the HPLC conditions are the same as in Example 3. The HPLC chromatograms for both products were virtually indistinguishable.

EXAMPLE 5

Synthesis of CC dimer using various aromatic carboxylic acids as activators

The comparative acidity of carboxylic acids was measured by preparing 0.05 M solutions in water and then measuring the pH of the resulting solutions. The activity of these carboxylic acids were measured by using them to activate the 5'-dimethoxytrityl-$N^4$-benzoyldeoxycytidine-3'-N,N'-diisopropylamino-β-cyanoethylphosphoramidite and then using the activated nucleotide reagent to form a CC dimer upon reaction with support-bound deoxycytidine. The coupling yield was quantitated by releasing the dimethoxytrityl group of the dimer and subsequently measuring the absorbance at 500 nm. For the purpose of comparison, CC dimer was synthesized using tetrazole; however, 0.5 M tetrazole was used instead of the 0.05 M solutions used in the case of carboxylic acids.

The results are reported in Table I.

TABLE I

| Activator | pH (0.05 M solution in water) | DMT % |
|---|---|---|
| Tetrazole | 3.04 | 98.6 |
| 2-nitrobenzoic acid | 1.69 | 42.12 |
| 3,5-dinitrobenzoic acid | 2.0 | 75.36 |
| 2,4,5-trifluorobenzoic acid | 2.19 | 14.74 |
| 2,3,6-trifluorobenzoic acid | 1.69 | 49.61 |
| Pentafluorobenzoic acid | 1.53 | 75.05 |
| Isobutyric acid | 3.02 | 14.03 |
| 2,3,5,6-tetrafluorobenzoic acid | 1.57 | 75.54 |
| Benzoic acid | 2.72 | 12.73 |
| Dichloroacetic acid | 1.33 | 85.02 |
| Trichloroacetic acid | 1.19 | 29.67 |
| Acetic acid | 2.84 | 12.13 |
| 2,4-dinitrobenzoic acid | 1.46 | 98.7 |
| 3-Nitrobenzoic acid | 1.64 | 13.16 |
| Trimethylacetic acid | 3.03 | 12.89 |

EXAMPLE 6

Melting temperature study of oligonucleoside methylphosphonates

The following methylphosphonate sequence was synthesized using tetrazole or 2,4-dinitrobenzoic acid:

5' TACTGTAGGCAGTACGAGAGT 3'    (SEQ ID NO:3).

The complementary oligonucleotide sequence was also synthesized:

5' ACTCTCGTACTGCCTACAGTA 3'    (SEQ ID NO:5).

A mixture of 0.5 $OD_{260nm}$ each of oligonucleoside methylphosphonate and its complement (normal oligonucleotide) was prepared in 1 ml 10 mM Tris, pH 7.5. Each sample was boiled for 10–15 minutes. The samples were allowed to cool very slowly in a water bath or a lead heating block. The samples were placed in a cuvette and the absorbance followed at 260 nm from 25° C. to 70° C., by raising the cuvette holder temperature 3 degrees at a time, and allowing the cuvette to stabilize for 3 minutes before taking an absorbance reading. The melting point curves obtained with tetrazole or 2,4-dinitrobenzoic acid are identical to each other within the limitations of experimental error.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and any specific terms employed herein are intended in a descriptive sense and not for purposes of limitation.

What is claimed is:

1. A composition comprising a secondary amine and an in situ generated compound of formula Ia or Ib:

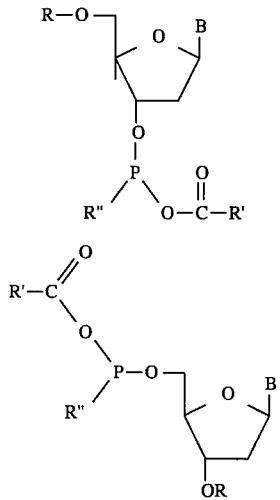

wherein: B is a purine or pyrimidine base; R is a hydroxyl-protecting group; R' is a substituted aryl; R" is selected from the group consisting of lower alkyl, lower alkoxy, NCCH$_2$CH$_2$O—, NCCH$_2$CH$_2$MeO—, NCCH$_2$CMe$_2$O—, Cl$_3$CCH$_2$O—, Cl$_3$CCMe$_2$O—, C$_6$H$_5$SO$_2$CH$_2$CH$_2$O—, MeSO$_2$CH$_2$CH$_2$O—, and NO$_2$C$_6$H$_4$CH$_2$CH$_2$O—.

2. The composition according to claim 1 wherein R' is an aryl group bearing at least one electron-withdrawing substituent which does not interfere with oligonucleotide synthesis.

3. The composition of claim 2, wherein aryl is selected from the group consisting of phenyl, naphthyl, and anthracyl.

4. The composition of claim 2, wherein the electron-withdrawing substitutent is selected from the group consisting of halogen or nitro.

5. The composition of claim 1, wherein R' is selected from the group consisting of 2-nitrophenyl; 3,5-dinitrophenyl; 2,4,5-trifluorophenyl; 2,3,6-trifluorophenyl; 2,3,5,6,-tetrafluorophenyl; pentafluorophenyl; 3-nitrophenyl; and 2,4-dinitrophenyl.

6. The composition of claim 5, wherein R' is 2,4-dinitrophenyl.

7. The composition of claim 1, wherein R" is selected from the group consisting of lower alkoxy, NCCH$_2$CH$_2$O—, NCH$_2$CH$_2$MeO—, NCCH$_2$CMe$_2$O—, Cl$_3$CCH$_2$O—, Cl$_3$CCMe$_2$O—, C$_6$H$_5$SO$_2$CH$_2$CH$_2$O—, MeSO$_2$CH$_2$CH$_2$O—, and NO$_2$C$_6$H$_4$CH$_2$CH$_2$O—.

8. The composition of claim 1, wherein R" is lower alkyl.

9. The composition of claim 1, wherein R is selected from the group consisting of 4,4'-dimethoxytrityl; 4,4',4"-tris-(benzyloxy)trityl; 4,4',4"-tris-(4,5-dichlorophthalimido)trityl; 4,4',4"-tris-(levulinyloxy)trityl; 3-(imidazolylmethyl)-4,4',-dimethoxytrityl; pixyl(9-phenylxanthen-9-yl); 9-(p-methoxyphenyl)xanthen-9-yl); 4-decyloxytrityl; 4-hexadecyloxytrityl; 9-(4-octadecyloxyphenyl)xanthene-9-yl; 1,1-bis-(4-methoxyhenyl)-1'-pyrenyl methyl; p-phenylazophenyloxycarbonyl; 9-fluorenylmethoxycarbonyl; 2,4-dinitrophenylethoxylcarbonyl; 4-(methylthiomethoxy)butyryl; 2-(methylthiomethoxymethyl)-benzoyl; 2-(isopropylthiomethoxymethyl)benzoyl; 2-(2,4-dinitrobenzenesulphenyloxymethyl)benzoyl; and levulinyl.

10. The composition of claim 9, wherein R is dimethoxytrityl.

11. The composition of claim 1, wherein B is selected from the group consisting of adenine, guanine, cytosine, and thymine.

12. A process for the preparation of the composition according to claim 1 containing the in situ genereated compound of formulae Ia or Ib comprising:

reacting the compound of either formula IIa or IIb

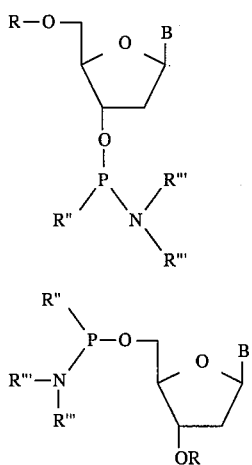

IIa

IIb wherein R and R" are defined as above and each R'" is lower alkyl or when taken together form the group —(CH$_2$)$_2$—O—(CH$_2$)$_2$— with an acid of general formula R'—C—OH in a suitable solvent.

13. In a process of oligonucleotide synthesis in which nucleoside phosphoramidite monomer precursors are activated by reaction with an activating agent to form activated intermediates and the activated intermediates are sequentially added to form an oligonucleotide product, wherein the improvement comprises using an substituted aryl carboxylic acid as the acid catalyst and thus generating in situ the compound of formula Ia or Ib according to claim 1.

* * * * *